(12) United States Patent
Linsi

(10) Patent No.: US 11,298,146 B2
(45) Date of Patent: Apr. 12, 2022

(54) ACTUATION MECHANISM WITH ARCUATE LEVERS

(71) Applicant: Alcon Inc., Fribourg (CH)

(72) Inventor: Thomas Linsi, Schaffausen (CH)

(73) Assignee: Alcon Inc., Fribourg (CH)

( * ) Notice: Subject to any disclaimer, the term of this patent is extended or adjusted under 35 U.S.C. 154(b) by 55 days.

(21) Appl. No.: 16/751,363

(22) Filed: Jan. 24, 2020

(65) Prior Publication Data

US 2020/0246034 A1 Aug. 6, 2020

Related U.S. Application Data (60) Provisional application No. 62/799,785, filed on Feb. 1, 2019.

(51) Int. Cl.
*A61B 17/29* (2006.01)
*A61B 17/3201* (2006.01)
(Continued)

(52) U.S. Cl.
CPC .......... *A61B 17/29* (2013.01); *A61B 17/3201* (2013.01); *A61B 2017/00862* (2013.01);
(Continued)

(58) Field of Classification Search
CPC . A61B 17/2841; A61B 17/29; A61B 17/2909; A61B 17/3201;
(Continued)

(56) References Cited

U.S. PATENT DOCUMENTS 5,147,378 A * 9/1992 Markham ............. A61B 17/29
294/100
5,549,627 A * 8/1996 Kieturakis ............. A61B 17/29
606/206

(Continued)

FOREIGN PATENT DOCUMENTS

DE 3526821 A1 2/1987
EP 0709063 A1 5/1996
(Continued)

OTHER PUBLICATIONS

Aktive Catalog 2016, pp. 8-9 with covers (4 pages).
(Continued)

*Primary Examiner* — Martin T Ton (57) ABSTRACT

Particular embodiments disclosed herein provide a surgical instrument comprising a device having a functional end configured to be inserted into a body part, a shaft coupled to a proximal end of the device, and a shaft housing configured to receive a distal end of the shaft and operable to move along a central axis of the shaft. The surgical instrument further comprises a tube coupled to the distal end of the shaft housing and configured to partially house the device such that the functional end of the device at least partially extends beyond the distal end of the tube. The surgical instrument further comprises a plurality of arcuate levers such that pressing one or more of the plurality of arcuate levers moves the shaft housing and the tube toward the functional end of the device, causing the tube to transition the device from a deactivated state to an activated state.

20 Claims, 5 Drawing Sheets

(51) Int. Cl.
*A61B 17/00* (2006.01)
*A61F 9/007* (2006.01)

(52) U.S. Cl.
CPC ............... *A61B 2017/00867* (2013.01); *A61B 2017/00955* (2013.01); *A61B 2017/2932* (2013.01); *A61F 9/007* (2013.01)

(58) Field of Classification Search
CPC .... A61B 2017/2845; A61B 2017/2912; A61B 2017/2918; A61B 2017/2924; A61B 2017/2932; A61B 2017/305; A61B 9/007; A61B 9/00736; A61B 2090/034
See application file for complete search history.

(56) References Cited

U.S. PATENT DOCUMENTS

| | | | |
|---|---|---|---|
| 6,482,198 | B1 | 11/2002 | Overaker |
| 6,488,695 | B1 | 12/2002 | Hickingbotham |
| 8,012,146 | B2 | 9/2011 | Hickingbotham |
| 8,187,293 | B2 | 5/2012 | Kirchhevel |
| 9,149,389 | B2 | 10/2015 | Scheller |
| 9,173,772 | B1 | 11/2015 | Scheller |
| 9,226,762 | B2 | 1/2016 | Scheller |
| 9,247,951 | B1 | 2/2016 | Scheller |
| 9,428,254 | B1 | 8/2016 | Scheller |
| 9,480,598 | B2 | 11/2016 | Clauson |
| 9,782,189 | B2 | 10/2017 | Scheller |
| 9,795,506 | B2 | 10/2017 | Scheller |
| 10,092,168 | B1 | 10/2018 | Huttner |
| 2002/0156465 | A1* | 10/2002 | Overaker ........... A61B 17/2909 606/1 |
| 2002/0161398 | A1* | 10/2002 | Hickingbotham .......................... A61B 17/2909 606/206 |
| 2003/0171762 | A1 | 9/2003 | Forchette |
| 2006/0089661 | A1* | 4/2006 | Dodge ............... A61B 17/2909 606/166 |
| 2007/0185514 | A1 | 8/2007 | Kirchhevel |
| 2012/0116435 | A1* | 5/2012 | Nallakrishnan ........ A61B 17/30 606/174 |
| 2014/0031844 | A1* | 1/2014 | Kusleika ........ A61B 17/320783 606/159 |
| 2014/0142603 | A1 | 5/2014 | Scheller |
| 2014/0379024 | A1* | 12/2014 | Schaller .............. A61F 9/00727 606/210 |
| 2015/0173944 | A1 | 6/2015 | Linsi |
| 2017/0079675 | A1 | 3/2017 | Scheller |
| 2017/0086871 | A1 | 3/2017 | Scheller |
| 2017/0156748 | A1 | 6/2017 | Scheller |
| 2017/0361034 | A1 | 12/2017 | Scheller |
| 2018/0000643 | A1 | 1/2018 | Scheller |
| 2018/0014849 | A1 | 1/2018 | Scheller |
| 2018/0193192 | A1 | 7/2018 | Charles |
| 2018/0235594 | A1 | 8/2018 | Scheller |
| 2019/0247229 | A1 | 8/2019 | Abt |

FOREIGN PATENT DOCUMENTS

| | | |
|---|---|---|
| JP | 5568016 B2 | 8/2014 |
| WO | WO0230302 A1 | 4/2002 |
| WO | WO2017066026 A1 | 4/2017 |
| WO | WO2017218161 A1 | 12/2017 |
| WO | WO2018017296 A1 | 1/2018 |
| WO | WO2018156341 A1 | 8/2018 |

OTHER PUBLICATIONS

Alcon Vitreoretinal Product Catalog, Section "Hand-Held Instrumentation", copyright 2008; Nov. 2009 Update, pp. 39-52.
https://web.archive.org/web/20181217182456/http://www.katalystsurgical.com/—Ophthalmic Instruments & Eye Instruments from KatalystSurgical.com, web archive dated Dec. 17, 2018 (2 pages).
Oertli Catalog 2018, pp. 41-47 with covers (9 pages).

* cited by examiner

ACTUATION MECHANISM WITH ARCUATE LEVERS

TECHNICAL FIELD

The present disclosure relates generally to a surgical instrument having an actuation mechanism including resilient, arcuate levers.

BACKGROUND

During certain surgical procedures (e.g., ophthalmic procedures) a surgeon is required to manipulate (e.g., remove, cut, peel, etc.) certain tissues within a body part by using forceps, scissors, etc. Examples of such surgical procedures are internal limiting membrane (ILM) removal and epiretinal membrane (ERM) removal for treating different macular surface diseases. During such procedures, a surgeon inserts the tip of a surgical instrument, which, for example, functions as forceps, into a patient's eye globe and uses the forceps to grasp and peel the ILM/ERM. Certain designs are currently used for providing a surgical instrument with an actuation mechanism that allows a surgeon to close and open the jaws of the forceps or scissors, which are located at the tip of a surgical instrument. However, in certain cases, the existing actuation mechanisms involve too many parts, are structurally complicated, and/or are difficult to assemble.

BRIEF SUMMARY

The present disclosure relates generally to a surgical instrument having an actuation mechanism including resilient, arcuate levers.

Particular embodiments disclosed herein provide a surgical instrument comprising a device comprising having a functional end configured to be inserted into a body part. In particular embodiments, the functional end may comprise forceps or scissors. In particular embodiments, the surgical instrument further comprises a shaft coupled to a proximal end of the device, and a shaft housing configured to receive a distal end of the shaft and operable to move along a central axis of the shaft. The surgical instrument further comprises a tube coupled to the distal end of the shaft housing and configured to partially house the device such that the functional end of the device at least partially extends beyond the distal end of the tube. The surgical instrument further comprises a plurality of arcuate levers, each arcuate lever having a proximal end coupled to the shaft and a distal end coupled to the shaft housing. Pressing one or more of the plurality of arcuate levers moves the shaft housing and tube toward the functional end the device, causing the tube to transition the device from a deactivated state to an activated state, such as closing the jaws of a pair of forceps if the functional end of device comprises forceps.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Particular embodiments of the present disclosure provide a surgical instrument having an actuation mechanism including resilient, arcuate levers.

Figure 1:
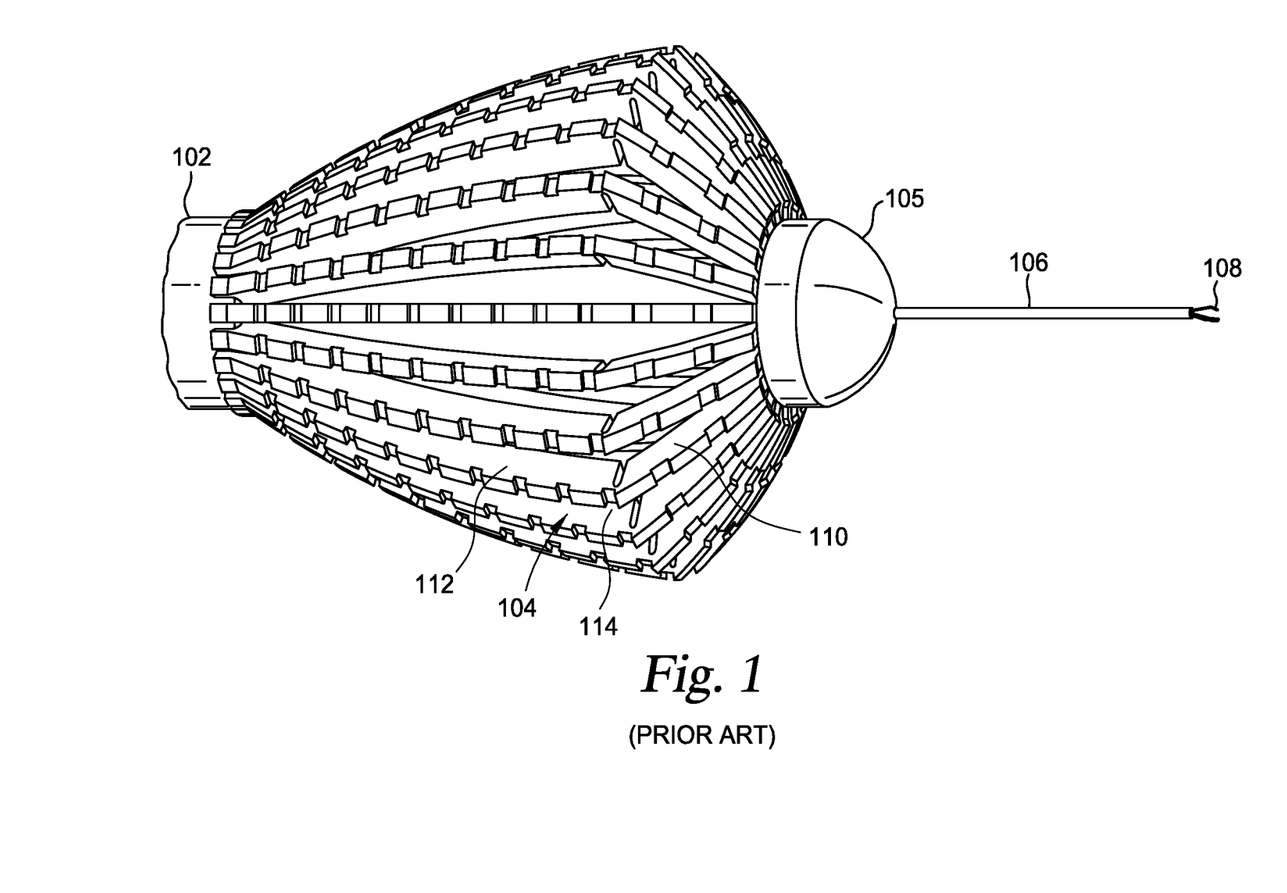
FIG. 1 illustrates an example of a surgical instrument with a prior art actuation mechanism.

FIG. 1 illustrates an example of a surgical instrument with a prior art actuation mechanism. As shown, surgical instrument 100 comprises a handle 102, a plurality of actuation levers 104, a housing 105, an actuation tube 106, and a device, shown as forceps 108, at the tip of the probe. Each actuation lever 104 is a single piece comprising a first leg 112 and a second leg 110 joined at flexible juncture 114. In other embodiments, the first leg 112 and second leg 110 may be separate pieces coupled together with a hinge. Each actuation lever 104 may be made from shape memory material, such as titanium, stainless steel or suitable thermoplastic. Actuation tube 106 may be any suitable medical grade tubing, such as titanium, stainless steel, or suitable polymer and is sized so that forceps 108 reciprocate easily within. Forceps 108 are generally made from stainless steel or titanium, but other materials may also be used.

Surgical instrument 100 is designed so that in use, when the plurality of actuation levers 104 is in its relaxed state, forceps 108 protrude or extend beyond the distal end of actuation tube 106, which is coupled to a housing 105. Squeezing one or more of the actuation levers 104 causes the respective actuation lever 104 to flex at juncture 114, pushing housing 105 forward relative to handle 102. The forward movement of housing 105 is transferred to actuation tube 106, causing actuation tube 106 to slide forward over a distal portion of the jaws of forceps 108, thereby activating forceps 108 by compressing together the jaws. By closing jaws of forceps 108, the surgeon is able to, for example, grasp and peel a tissue (e.g., ILM) within a body part.

In the example of FIG. 1, actuation levers 104 may be structurally complicated and/or difficult to assemble. Accordingly, certain embodiments described herein relate to an actuation handle with an actuation mechanism including arcuate levers. In particular embodiments, this may reduce the structural complexity of the actuation mechanism and allow for easier assembly.

Figure 2:
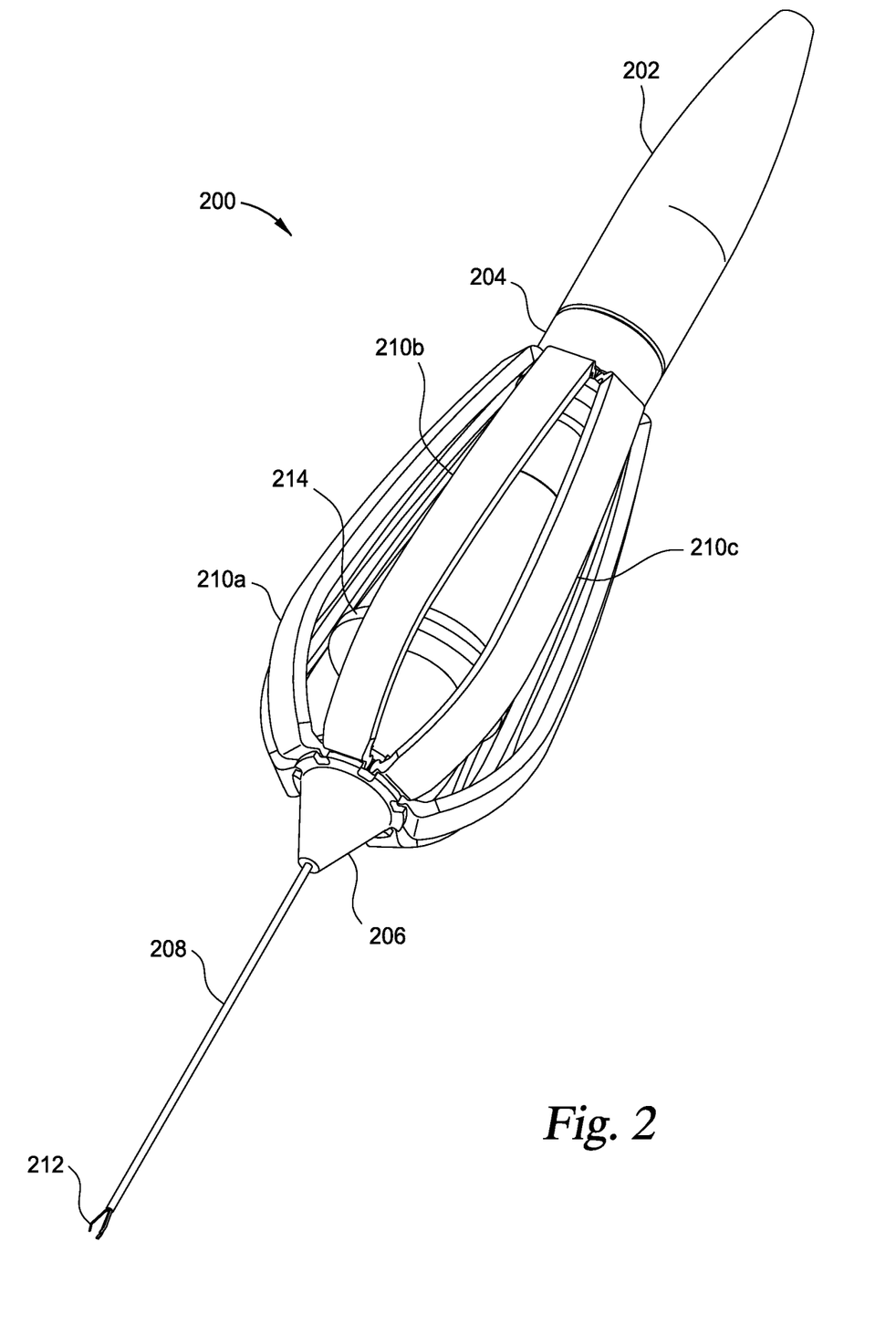
FIG. 2 illustrates an outside view of an example surgical instrument, according to some embodiments of the present disclosure.

FIG. 2 illustrates an outside view of an example surgical instrument 200 in accordance with the teachings of the present disclosure. As shown in FIG. 2, surgical instrument 200 comprises a rear cap 202, a shaft 204, a shaft housing 206, an actuation tube 208, a stop ring 214, a plurality of levers 210 (e.g., 210a, 210b, 210c, etc.), and a device 212.

Figure 4:
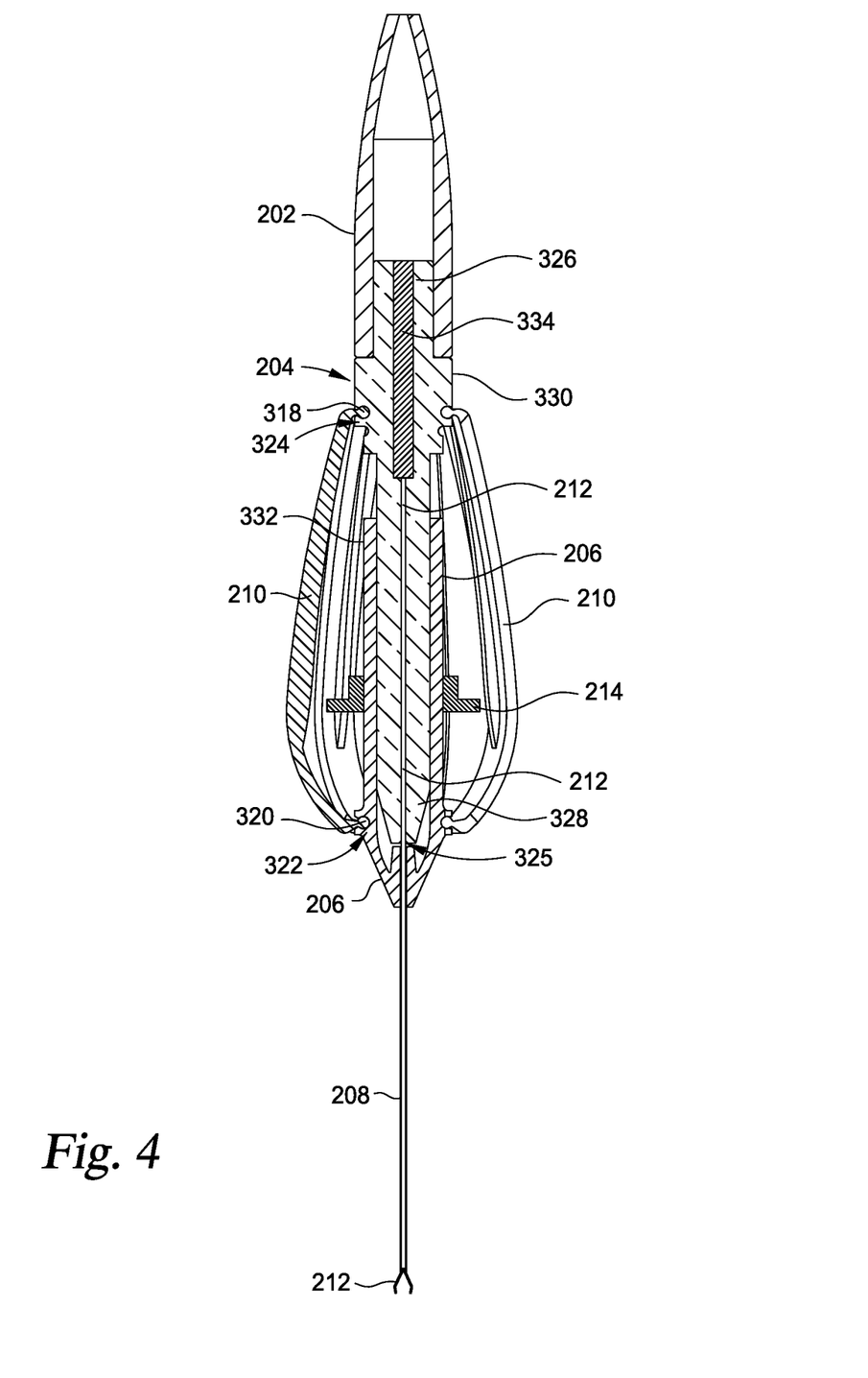
FIG. 4 illustrates a cross-sectional view of the surgical instrument of FIG. 2, in a deactivated state.
Figure 5:
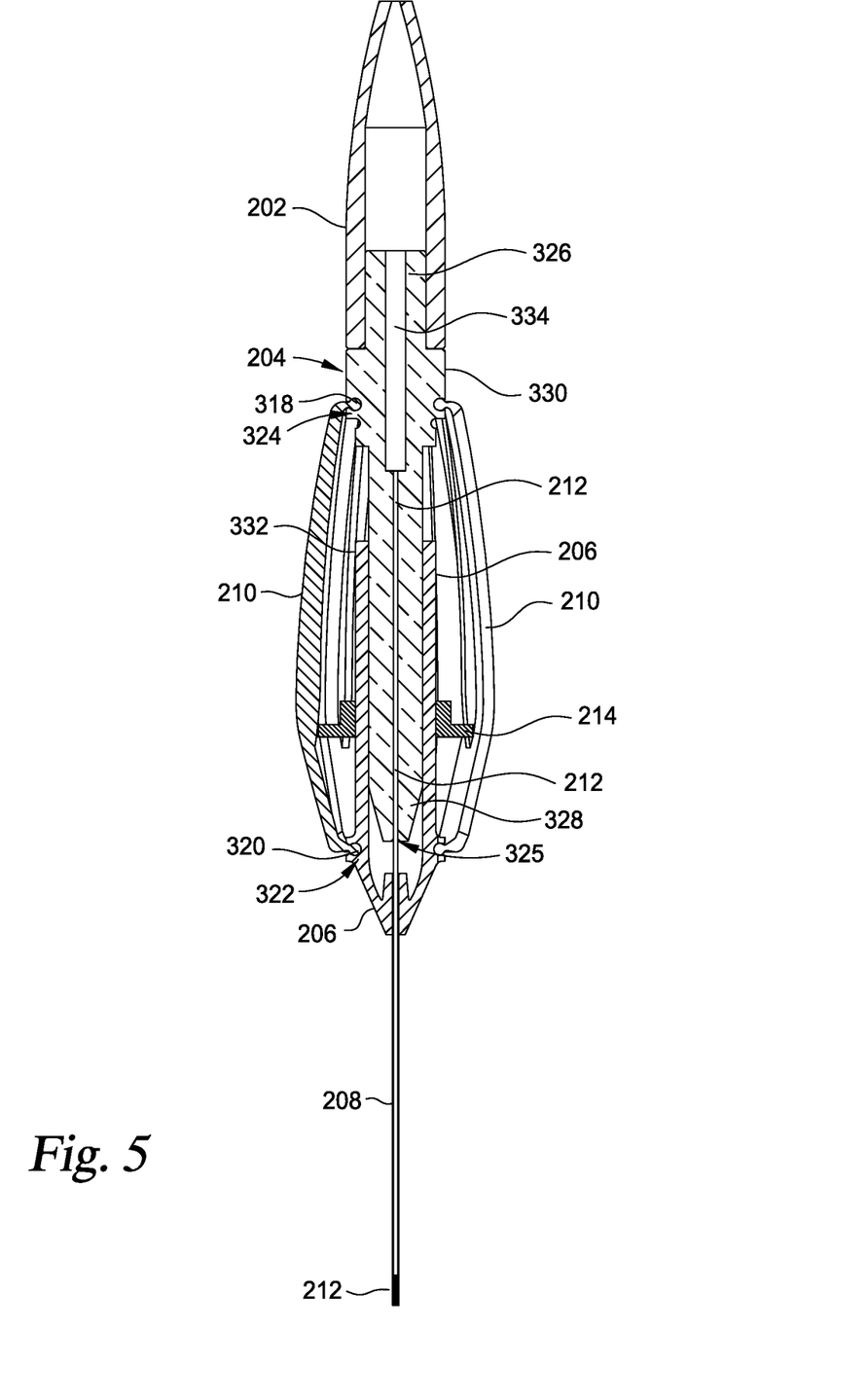
FIG. 5 illustrates a cross-sectional view of the surgical instrument of FIG. 2 in an activated state.

Device 212 may be any surgical device that is shaped to fit in tube 208 with a distal end that is referred to as a functional end (e.g., a movable or active end). For example, device 212 may be shaped as a needle with a functional end, which may comprise forceps, scissors, etc., with jaws or arms. The proximal end (not shown) of device 212 is coupled to shaft 204, as shown in FIGS. 4 and 5.

Levers 210 are coupled to shaft housing 206 at their distal ends and to shaft 204 at their proximal ends. Each lever 210 has a generally arcuate shape such that the middle of each lever 210 is further away from shaft 204 and shaft housing 206 than the distal and proximal ends of the respective lever. Levers 210 are formed of resilient material (e.g., flexible and/or springy material) such that, when pressed inward toward shaft 204, levers 210 flex, but revert back to their at-rest positions when they are released. In certain embodiments, levers 210 are formed of polycarbonate, polyetheretherketone (PEEK), or similar thermoplastic material. Unlike the prior art levers 104 shown in FIG. 1, levers 210 are not configured to flex at a discontinuity (e.g., junction 114 in FIG. 1). Instead, levers 210 are configured to flex similar to leaf springs. When a lever 210 is pressed inward towards shaft 204, the compression of the lever causes the lever 210 to transition from a first, steeper curvature to a second, shallower curvature, in the process moving the distal end of the lever 210 towards the distal end of instrument 200. Surgical instrument 200 is designed so that in use, when levers 210 are in their relaxed or at-rest state, the functional end of device 212 protrudes or extends beyond the distal end of tube 208. Note that FIG. 2 illustrates levers 210 in their at-rest or deactivated position while FIG. 5 illustrates levers 210 in their pressed or activated position.

When levers 210 are pressed, they push shaft housing 206 forward relative to shaft 204 and device 208. The forward movement of shaft housing 206 is transferred to tube 208, causing tube 208 to slide forward and activate device 212. Device 212 is activated as a result of the forward movement of tube 206, which presses the jaws or arms of device 212 together. An activated device refers to a device whose jaws or arms are closed. As shown, a stop ring 214 may be coupled to or placed around shaft housing 206 to limit the movement of levers 210 towards shaft housing 206. In other words, stop ring 214 prevents levers 210 from over extending (e.g., becoming completely flat) when, for example, a user applies too much pressure on them.

Levers 210, shaft housing 206, stop ring 214, shaft 204, and tube 208 may be collectively referred to as an actuation handle that is configured to activate and deactivate device 212 of surgical instrument 100. In the example of FIG. 2, surgical instrument 200 comprises seven levers 210. However, a fewer or larger number of levers 210 may be used in other embodiments.

Figure 3:
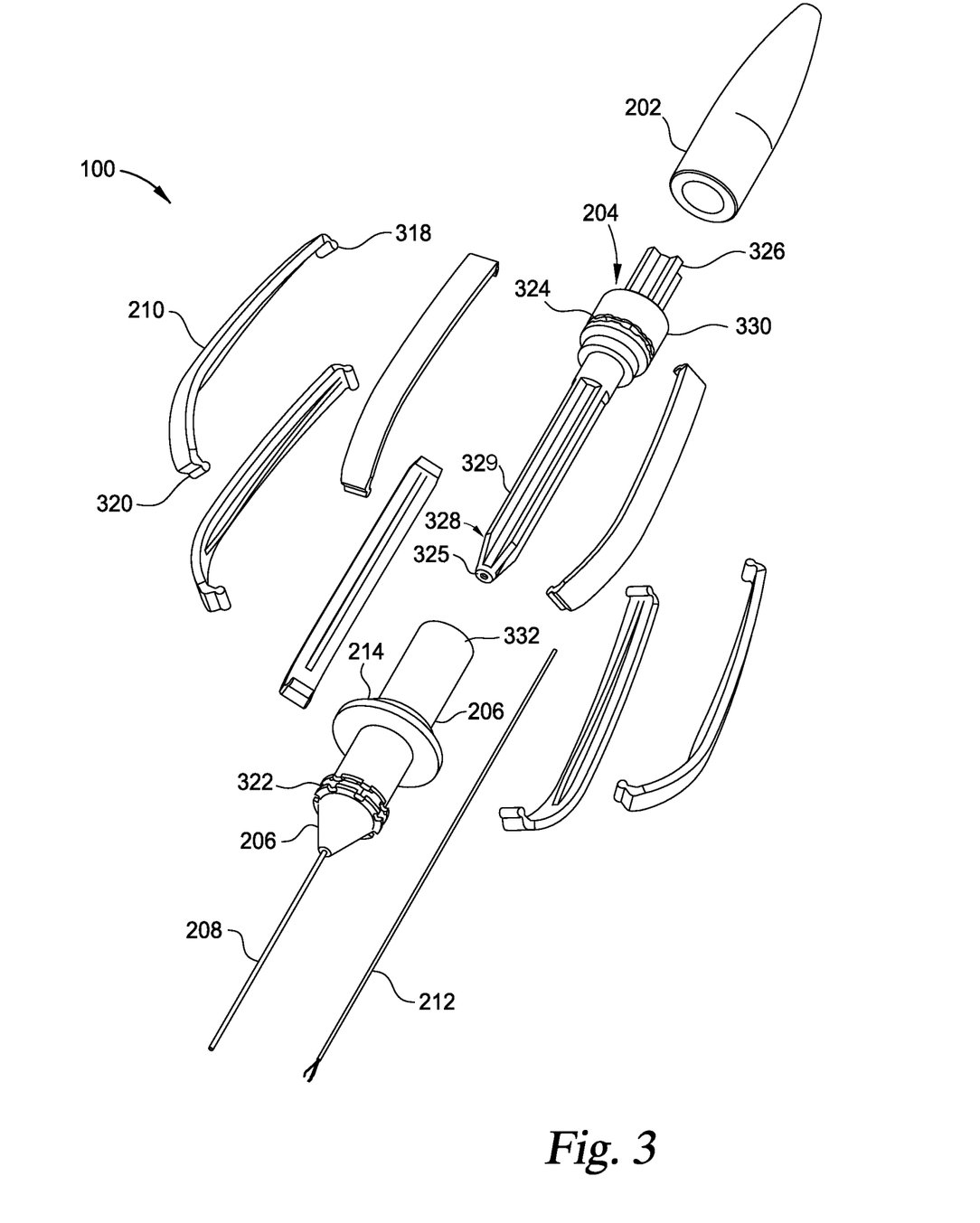
FIG. 3 illustrates an exploded view of the surgical instrument of FIG. 2.

FIG. 3 illustrates an exploded view of surgical instrument 200 of FIG. 2. As shown in FIG. 3, a proximal end 326 of shaft 204 is coupled to (e.g., press-fitted or inserted into) rear cap 202 while a distal end 328 of shaft 204 is inserted into the shaft housing 206. Shaft 204 also comprises a central element 330 that a distal end 332 of shaft housing 206 may, in certain embodiments, make contact with when levers 210 are relaxed (e.g., when device 212 is in the deactivated state). In such embodiments, when levers 210 are pressed, shaft housing 206 slides forward relative to shaft 204 such that distal end 332 of shaft 204 and central element 330 no longer touch. In other embodiments, distal end 332 of shaft housing 206 and central element 330 never touch even when levers 210 are relaxed.

As shown in FIG. 3, each lever 210 includes a lever tail 318 at its proximal end and a lever head 320 at its distal end. Each lever tail 318 is configured to couple the respective lever 210 to central element 330, and each lever head 320 is configured to couple the respective lever 210 to shaft housing 206. In particular embodiments, this coupling may be accomplished by having each lever tail and/or lever head mate with a corresponding housing on the central element 330 or shaft housing 206. For example, as illustrated in FIG. 3, central element 330 comprises a plurality of tail housings 324, each configured to house a lever tail 318 of a lever 210. In particular embodiments, each lever tail 318 may have a cylindrical shape and the corresponding tail housing 324 may comprise a u-shaped groove that is configured to house the cylindrical lever tail 318. In such an embodiment, a tail housing 324 and a lever tail 318 are coupled such that the lever tail 318 is able to rotate within and relative to the tail housing 324 when levers 210 are being pressed and released.

Similarly, as shown in FIG. 3, shaft housing 206 comprises a plurality of head housings 322, each configured to house a lever head 320 of a lever 210. More specifically, each head housing 322 comprises a u-shaped groove that is configured to house a lever head 320 that, similar to a lever tail 318, is also shaped somewhat similar to a cylinder. Further, a head housing 322 and a lever head 320 are coupled such that the lever head 320 is able to rotate within and relative to the head housing 322 when levers 210 are being pressed and released. Note that the cylindrical shapes of lever tail 318 and lever head 320 as well as the shapes of tail housing 324 and head housing 322 are merely exemplary. In other examples, any lever tail 318 and tail housing 324 as well as lever head 320 and head housing 322 may be of any suitable complementary shapes. Also, in certain embodiments, levers 210 may be coupled to shaft 204 and shaft housing 206 using other mechanisms. For example, lever tails 318 and shaft 204 may be coupled together using film hinges. In another example, film hinges may instead be used to couple lever heads 320 and shaft housing 206.

In particular embodiments, shaft 204 further comprises a tube- or tunnel-shaped passage 325 into which the proximal end of device 212 is configured to be partially inserted. As described above, device 212 is attached or coupled to shaft 204 such as to prevent device 212 from moving, longitudinally or otherwise, relative to shaft 204. As such, the proximal end of device 212 may be glued to the end of passage 325.

In particular embodiments, shaft 204 may comprise one or more protrusions 329 used for ensuring that shaft 204 does not rotate within and relative to shaft housing 206 when levers 210 are pressed. In the example shown in FIG. 3 shaft 204 has four such protrusions 329 (three of which are visible in the figure) extending radially from the shaft at uniform intervals. Because of protrusions 329, when viewed down its central axis, shaft 204 may have a cross-shaped cross-section. As shown in FIG. 3, shaft 204 comprises similar protrusions at its proximal end. In particular embodiments, protrusions 329 correspond to a plurality of receptacles (not illustrated) on the interior of shaft housing 206 into which protrusions 329 may be inserted. The interaction of protrusions 329 and these receptacles may help limit or prevent shaft 204 from rotating in relation to shaft housing 206 when levers 210 are pressed. Although shaft 204 has been described above as having four protrusions 329, in other embodiments shaft 204 may comprise other numbers and arrangements of protrusions.

FIG. 4 illustrates a cross-sectional view of surgical instrument 200 when levers 210 are in a relaxed or at-rest position, in accordance with a particular embodiment. As shown, proximal end 326 of shaft 204 is inserted into rear cap 204 while distal end 328 of shaft 204 is inserted into shaft housing 206. The proximal end of device 212 is coupled to a device housing 334 of shaft 204. Device housing 334 is a cylindrical element into which the proximal end of device 212 is partially inserted. In other examples, device housing 334 may be of any other suitable shape. As described above, the proximal end of device 212 and device housing 334 may be coupled together using adhesive material. In other embodiments, one of a plurality of other techniques may be used for coupling the proximal end of device 212 and device housing 334.

As shown, device 212 extends through passage 325 of shaft 204 as well as tube 208. When levers are relaxed, as is the case in the example of FIG. 4, the distal or functional end of device 212 extends beyond the distal end of tube 208. As a result, in the example of FIG. 4, device 212 is in a deactivated state. In certain embodiments, the arcuate length of levers 210 directly correspond to how far shaft housing 206 slides forward when levers 210 are pressed. The larger the arcuate length of levers 210 (e.g., the steeper the curve of levers 210), the further shaft housing 206 slides forward when levers 210 are pressed inward.

FIG. 5 illustrates a cross-sectional view of surgical instrument 200 when device 212 is in the activated state, in accordance with a particular embodiment. As shown, levers 210 flex when they are pressed inward toward shaft 204, transitioning from a first, steeper curvature to a second, shallower curvature and, as a result, move or push shaft housing 206 forward relative to shaft 204 and device 208. The forward movement of shaft housing 206 is transferred to tube 208, causing tube 208 to slide forward and activate device 212. As shown, relative to FIG. 4, shaft housing 206 has moved forward such that distal end 332 of shaft housing 206 is separated from central element 330 of shaft 204 by a larger distance. Further, the functional end of device 212 is activated because the jaws or arms are closed by the distal end of tube 208. When levers 210 are released, they transition back to their original curvature, pulling shaft housing 206 backward, causing tube 208 to deactivate the functional end of device 212 by opening the jaws or arms. As described above, because levers 210 are resilient, pressing them results a certain amount of spring force that causes levers 210 to revert back to their at-rest state when they are released.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A surgical instrument, comprising:
   a device having a functional end configured to be inserted into a body part;
   a shaft coupled to a proximal end of the device;
   a shaft housing having a proximal end configured to receive a distal end of the shaft and operable to move along a central axis of the shaft;
   a tube coupled to the distal end of the shaft housing and configured to partially house the device such that the functional end of the device at least partially extends beyond a distal end of the tube;
   a plurality of arcuate levers, each arcuate lever having a proximal end coupled to the shaft and a distal end coupled to the shaft housing such that pressing one or more of the plurality of arcuate levers moves the shaft housing and the tube toward the functional end of the device, causing the tube to transition the device from a deactivated state to an activated state;
   the proximal end of each of the plurality of arcuate levers comprises a lever tail configured to rotate within a tail housing of the shaft; and
   the distal end of each of the plurality of arcuate levers comprises a lever head configured to rotate within a head housing of the shaft housing;
   wherein pressing the one or more of the plurality of arcuate levers causes the lever tail and the lever head of each of the plurality of arcuate levers to rotate within the respective tail housing and head housing.

2. The surgical instrument of claim 1, wherein pressing at least one of the plurality of arcuate levers transitions the at least one of the plurality of arcuate levers from a first curvature to a second curvature, the second curvature being shallower than the first curvature.

3. The surgical instrument of claim 1, wherein:
   the functional end of the device comprises jaws or arms; and
   causing the tube to transition the device from the deactivated state to the activated state further comprises closing the jaws or arms.

4. The surgical instrument of claim 1, wherein the plurality of levers is formed of a resilient material.

5. The surgical instrument of claim 1, wherein the plurality of arcuate levers is formed of at least one of polycarbonate or polyetheretherketone (PEEK).

6. The surgical instrument of claim 1, wherein each of the plurality of arcuate levers extends when the lever is pressed.

7. The surgical instrument of claim 1, further comprising:
   a protrusion extending outward from the shaft housing configured to limit movement of the plurality of arcuate levers towards the shaft housing.

8. The surgical instrument of claim 7, wherein the protrusion comprises a stop ring.

9. The surgical instrument of claim 1, wherein releasing the one or more of the plurality of arcuate levers when the device is in the activated state causes the shaft housing and tube to move towards the proximal end of the device, causing the tube to transition the device from the activated state to the deactivated state.

10. A surgical instrument, comprising:
    a device having a functional end configured to be inserted into a body part;
    a shaft coupled to a proximal end of the device;
    a shaft housing having a proximal end configured to receive a distal end of the shaft and operable to move along a central axis of the shaft;
    a tube coupled to the distal end of the shaft housing and configured to partially house the device such that the functional end of the device at least partially extends beyond a distal end of the tube;
    a plurality of arcuate levers, each arcuate lever having a proximal end coupled to the shaft and a distal end coupled to the shaft housing such that pressing one or more of the plurality of arcuate levers moves the shaft housing and the tube toward the functional end of the device, causing the tube to transition the device from a deactivated state to an activated state;
    wherein:
    the shaft comprises a plurality of protrusions extending outward from the central axis of the shaft; and
    the shaft housing comprises a plurality of receptacles, each receptacle configured to receive one of the plurality of protrusions when the shaft is received by the shaft housing, such that interaction of the respective plurality of protrusions and plurality of receptacles limits rotation of the shaft relative to the shaft housing when the one or more of the plurality of arcuate levers are pressed.

11. The surgical instrument of claim 10, wherein pressing at least one of the plurality of arcuate levers transitions the at least one of the plurality of arcuate levers from a first curvature to a second curvature, the second curvature being shallower than the first curvature.

12. The surgical instrument of claim 10, wherein:
the functional end of the device comprises jaws or arms; and
causing the tube to transition the device from the deactivated state to the activated state further comprises closing the jaws or arms.

13. The surgical instrument of claim 10, wherein the plurality of levers is formed of a resilient material.

14. The surgical instrument of claim 10, wherein the plurality of arcuate levers is formed of at least one of polycarbonate or polyetheretherketone (PEEK).

15. The surgical instrument of claim 10, wherein:
the proximal end of each of the plurality of arcuate levers comprises a lever tail configured to rotate within a tail housing of the shaft; and
the distal end of each of the plurality of arcuate levers comprises a lever head configured to rotate within a head housing of the shaft housing.

16. The surgical instrument of claim 15, wherein pressing the one or more of the plurality of arcuate levers causes the lever tail and the lever head of the each of the plurality of arcuate levers to rotate within the respective tail housing and head housing.

17. The surgical instrument of claim 10, wherein each of the plurality of arcuate levers extends when the lever is pressed.

18. The surgical instrument of claim 10, further comprising:
a protrusion extending outward from the shaft housing configured to limit movement of the plurality of arcuate levers towards the shaft housing.

19. The surgical instrument of claim 18, wherein the protrusion comprises a stop ring.

20. The surgical instrument of claim 10, wherein releasing the one or more of the plurality of arcuate levers when the device is in the activated state causes the shaft housing and tube to move towards the proximal end of the device, causing the tube to transition the device from the activated state to the deactivated state.

* * * * *